(12) United States Patent
Li et al.

(10) Patent No.: US 10,085,469 B2
(45) Date of Patent: Oct. 2, 2018

(54) METHOD AND APPARATUS FOR CONTROLLING A COOKING PROCESS OF FOOD

(71) Applicant: KONINKLIJKE PHILIPS N.V., Eindhoven (NL)

(72) Inventors: Wei Li, Eindhoven (NL); Bin Yin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 73 days.

(21) Appl. No.: 15/118,200

(22) PCT Filed: Mar. 11, 2015

(86) PCT No.: PCT/EP2015/054995
§ 371 (c)(1),
(2) Date: Aug. 11, 2016

(87) PCT Pub. No.: WO2015/140013
PCT Pub. Date: Sep. 24, 2015

(65) Prior Publication Data
US 2017/0127707 A1 May 11, 2017

(30) Foreign Application Priority Data

Mar. 17, 2014 (WO) ................ PCT/CN2014/000274
May 30, 2014 (EP) ..................................... 14170633

(51) Int. Cl.
*A23L 5/10* (2016.01)
*G01N 27/02* (2006.01)
(Continued)

(52) U.S. Cl.
CPC .................. *A23L 5/10* (2016.08); *A23L 5/36* (2016.08); *G01N 22/00* (2013.01); *G01N 27/026* (2013.01);
(Continued)

(58) Field of Classification Search
CPC ...... A23L 5/10–5/19; A23L 5/30–5/36; G01N 22/00; G01N 33/02–33/12; G01N 27/026; H05B 6/6447; H05B 6/6467
(Continued)

(56) References Cited

U.S. PATENT DOCUMENTS

| 4,341,937 A | * | 7/1982 | Staats | ................. | H05B 6/6447 |
| | | | | | 219/709 |
| 4,520,250 A | * | 5/1985 | Ishihara | ............... | H05B 6/6411 |
| | | | | | 219/703 |

(Continued)

FOREIGN PATENT DOCUMENTS

| DE | 10306940 A1 | 9/2004 |
| JP | 5668361 A | 6/1981 |

OTHER PUBLICATIONS

Green, Aliza (2005), "Field Guide to Meat", Philadelphia, PA: Quirk Books. pp. 294-295. ISBN 1594740178.
(Continued)

*Primary Examiner* — Drew E Becker

(57) ABSTRACT

The present invention relates to a method and apparatus for controlling a cooking process of food. The method comprises a step of emitting (101) a plurality of radio frequency signals into the food non invasively. The method also comprises a step of receiving (105) a plurality of reflection signals or transmission signals of the radio frequency signals from the food, wherein the reflection signals is a part of the radio frequency signals that reflect from the food, and the transmission signals is a part of the radio frequency signals that transmit through the food. The method also comprises a step of obtaining (110) a protein status, wherein the protein status is the extent of protein denaturation, in the food in the course of heating the food based on the plurality of radio frequency signals and the plurality of reflection signals or transmission signals. The method also comprises a step of
(Continued)

determining (120) a doneness level of the food based on the protein status, and a step of controlling (130) the cooking process of the food based on the determined doneness level. Using the protein denaturation provides a more direct and precise information of the status of food based on established relation between the doneness level and the protein denaturation extent.

11 Claims, 9 Drawing Sheets

(51) Int. Cl.
  *G01N 22/00* (2006.01)
  *G01N 33/12* (2006.01)
  *H05B 6/64* (2006.01)
  *A23L 5/30* (2016.01)
(52) U.S. Cl.
  CPC ............ *G01N 33/12* (2013.01); *H05B 6/6467* (2013.01); *A23V 2002/00* (2013.01)
(58) Field of Classification Search
  USPC ......... 426/231–233, 241–243, 523; 219/704, 219/709, 750
  See application file for complete search history.

(56) References Cited

U.S. PATENT DOCUMENTS

| | | | |
|---|---|---|---|
| 2008/0137068 A1* | 6/2008 | Ouchi | ................ G01N 21/3581 356/51 |
| 2009/0311794 A1 | 12/2009 | Campbell | |
| 2009/0321428 A1* | 12/2009 | Hyde | ................... H05B 6/6455 219/702 |
| 2010/0187224 A1* | 7/2010 | Hyde | ..................... H05B 6/705 219/720 |
| 2012/0039356 A1 | 2/2012 | Adams | |
| 2013/0059037 A1 | 3/2013 | Heinz | |
| 2013/0080098 A1* | 3/2013 | Hadad | .................... G01N 27/00 702/66 |
| 2013/0092680 A1 | 4/2013 | Cartwright | |
| 2013/0142923 A1* | 6/2013 | Torres | .................... H05B 6/705 426/233 |
| 2013/0306626 A1 | 11/2013 | Torres | |
| 2014/0348987 A1* | 11/2014 | Cheng | .................... A47J 27/04 426/231 |
| 2016/0128138 A1* | 5/2016 | Li | .......................... H05B 6/688 219/707 |

OTHER PUBLICATIONS

Hamm, R. (1966), "Heating of muscle systems" In E. J. Briskey, R. G. Cassens, & J. C. Trautman (Eds.), The physiology and biochemistry of muscle as a food (p. 363). Madison: University of Wisconsin Press.

* cited by examiner

METHOD AND APPARATUS FOR CONTROLLING A COOKING PROCESS OF FOOD

This application is the U.S. National Phase application under 35 U.S.C. § 371 of International Application No. PCT/EP2015/054995, filed on Mar. 11, 2015, which claims the benefit of International Application No. 14170633.3 filed on May 30, 2014 and International Application No. PCT/CN2014/000274 filed Mar. 17, 2014. These applications are hereby incorporated by reference herein.

FIELD OF THE INVENTION

The present technology relates to the field of cooking control, particularly to a method for controlling a cooking process of food at least based on detecting the doneness level of the food. The technology also relates to an apparatus, a cooking device and a computer readable storage medium for performing the method.

BACKGROUND OF THE INVENTION

Currently, home cooking control either relies on manual control by the user during cooking or preset parameters input by the user before cooking, such as food type, cooking time, temperature, etc. In the first case, mistakes of user may 'destroy' the food, e.g. overcooked. In the second case, manual input brings inconvenience and is still experience dependent, and furthermore a non optimal cooking result is often encountered due to a significant discrepancy between the actual food and the 'average' food model used by a cooking appliance.

Food doneness is largely associated with its core temperature. Currently, this is monitored invasively during cooking by inserting a needle shaped thermometer into the food. The method of detecting food doneness is destructive and moreover only provides temperature information of a particular part of the food which can not accurately represent the overall temperature in the food. Furthermore, the needle in the cooking machine will make the cooking machine difficult to clean. Meanwhile, in order to avoid damage the food seriously, it is often that a very thin needle is used. Such needle is so liable to broke or bend as to impact its usage. Also, the machine structure will be complicated with the added needle, which will also increase the product cost of the cooking machine.

US2013/0306626 A1 describes systems, apparatuses, and methods for food cooking using radio frequency.

US2013/0080098 A1 describes a device and method for applying electromagnetic energy in the radio frequency range to determine or detect a processing state of an object being processed.

US2013/0092680 describes an oven including a cooking chamber configured to receive a food product having a first and second energy sources, and a user interface configured to display information associated with processes for cooking. The oven may be employ feedback data regarding absorption of radio frequency spectrum.

SUMMARY OF THE INVENTION

It is an object of the present disclosure to solve or alleviate at least one of the problems mentioned above.

A first aspect of the present disclosure is a method for controlling a cooking process of food. The method comprising obtaining a protein status in the food in the course of heating the food, wherein the protein status is the extent of protein denaturation; determining a doneness level of the food based on the protein status; and controlling the cooking process of the food based on the determined doneness level. Furthermore, the method emits a plurality of radio frequency signals into the food noninvasively and receives a plurality of reflection signals or transmission signals of the radio frequency signals from the food. The reflection signals is a part of the radio frequency signals that reflect from the food, and the transmission signals is a part of the radio frequency signals that transmit through the food. Then, the method obtains the protein status based on the plurality of radio frequency signals and the plurality of reflection signals or transmission signals.

Protein is a good indicator representing the actual status of the food along a cooking process, because it is an important ingredient in the food (e.g., meat), meanwhile the protein status of the food is highly related to the food doneness during the cooking process. The actual indicator for doneness level is protein denaturation, i.e. the chemical status of the protein, which can provide more direct and precise information of the status of food based on established relation between the doneness level and the protein denaturation extent.

The advantages of the method are embodied in the following aspects. In the first aspect, the proposed method offers an automatic cooking solution in comparison with traditional methods that need user's input about target time/temperature. In this method, the user is only required to set a target doneness level of the food without inputting other cooking parameters such as temperature, cooking time etc, which is not easily grasped by an average user. As a result, it minimizes user intervention during cooking. In the second aspect, precise cooking control is enabled due to the direct indication of protein status during cooking. Temperature is a traditional indicator for cooking process. It is the cause of ingredient status change, but it is not the direct indicator of food status. In some cases, with salt, with different meat composition, with different personal preferences, and with different meat types, the temperature cannot give precise doneness information. By contrast, in this method, protein status is proposed as the indicator of food doneness, which facilitates to detect the food doneness more timely and accurately.

By involving the penetrative signal such as radio frequency signal in obtaining the protein status of the food, the food doneness can be determined in a non-invasive way. In this way, the integrity of the food will not be destroyed, thereby improving the visual experience when tasting the food.

Optionally, the plurality of radio frequency signals may have the same frequency. As such, the method may emit the plurality of radio frequency signals into the food at different points of time in the course of heating the food; obtain the protein status based on dielectric properties of the food, the dielectric properties are determined based on the phases or amplitudes of the radio frequency signals and the plurality of reflection signals or transmission signals; and determine the doneness level of the food based on the dielectric properties over time.

The change of dielectric property in food is featured by staged drop and rise associated with food doneness levels, which makes the determination of the doneness level of the food independent of the absolute measurement value, thereby protecting the determination of the doneness level against disturbing factors such as initial status of the food, composition variance in the food. This is an apparently advantage by comparison with measuring temperature (monotonically increasing) or moisture loss (monotonically decreasing).

Optionally, the plurality of radio frequency signals may have at least two frequencies. As such, the method may emit the plurality of radio frequency signals into the food; extract parameters indicating the protein status in the food based on the plurality of radio frequency signals and the plurality of reflection signals or transmission signals; and determine the doneness level of the food based on the extracted parameters.

The introduction of multi-frequency information makes the sensing more robust against various disturbing factors including measurement error, electronic noise and food variation. Therefore, the food doneness can be determined accurately.

A second aspect of the present disclosure is an apparatus configured to control a cooking process of food. The apparatus comprises an emitting unit, a receiving unit, an obtaining unit, a determining unit and a controlling unit. The emitting unit is adapted to emit a plurality of radio frequency, radio frequency signals into the food noninvasively. The receiving unit is adapted to receive a plurality of reflection signals or transmission signals of the radio frequency signals from the food. The reflection signals is a part of the radio frequency signals that reflect from inside of the food. The transmission signals is a part of the radio frequency signals that transmit through the food. The obtaining unit is adapted to obtain a protein status in the food in the course of heating the food based on the plurality of radio frequency signals and the plurality of reflection signals or transmission signals, wherein the protein status is the extent of protein denaturation. The determining unit adapted to determine a doneness level of the food based on the protein status; and the controlling unit adapted to control the cooking process of the food based on the determined doneness level.

A third aspect of the present disclosure is a cooking device. The cooking device comprises an apparatus configured to detect doneness of food as described above.

A fourth aspect of the present disclosure is a computer readable storage medium storing instructions. When executed on an apparatus, the instructions cause the apparatus to perform the steps of the method as described above.

BRIEF DESCRIPTION OF THE DRAWINGS

The technology will now be described, by way of example, based on embodiments with reference to the accompanying drawings, wherein.

DETAILED DESCRIPTION OF EMBODIMENTS

Figure 1:
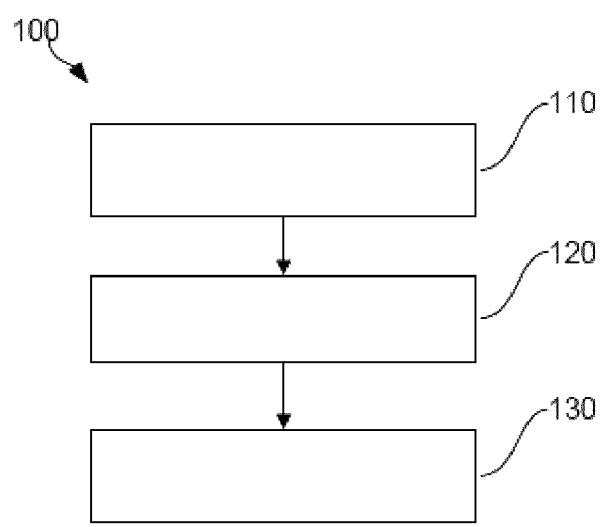
FIG. 1 schematically illustrates a flowchart of a method for controlling a cooking process of the food in accordance with an embodiment.

Embodiments herein will be described more fully hereinafter with reference to the accompanying drawings. The embodiments herein may, however, be embodied in many different forms and should not be construed as limiting the scope of the appended claims. The elements of the drawings are not necessarily to scale relative to each other. Like numbers refer to like elements throughout.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood. It will be further understood that terms used herein should be interpreted as having a meaning that is consistent with their meaning in the context of this specification and the relevant art and will not be interpreted in an idealized or overly formal sense unless expressly so defined herein.

The present technology is described below with reference to block diagrams and/or flowchart illustrations of methods, apparatus (systems) and/or computer program according to the present embodiments. It is understood that blocks of the block diagrams and/or flowchart illustrations, and combinations of blocks in the block diagrams and/or flowchart illustrations, may be implemented by computer program instructions. These computer program instructions may be provided to a processor, controller or controlling unit of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

Accordingly, the present technology may be embodied in hardware and/or in software (including firmware, resident software, micro-code, etc.). Furthermore, the present technology may take the form of a computer program on a computer-usable or computer-readable storage medium having computer-usable or computer-readable program code embodied in the medium for use by or in connection with an instruction execution system. In the context of this document, a computer-usable or computer-readable storage medium may be any medium that may contain, store, or is adapted to communicate the program for use by or in connection with the instruction execution system, apparatus, or device.

Embodiments herein will be described below with reference to the drawings.

Taking beef steak cooking as example, the core temperature may be used as the indicator of beef steak doneness. As illustrated in the table below, the doneness of the beef steak is divided into a plurality of doneness levels. The individual doneness levels correspond to the respective temperature ranges.

| Doneness level | Description | Temperature range |
| --- | --- | --- |
| Extra-rare or Blue | very red and cold | 46-49° C. |
| Rare | cold red center; soft | 52-55° C. |
| Medium rare | warm red center; firmer | 55-60° C. |
| Medium | pink and firm | 60-65° C. |
| Medium well | small amount of pink in the center | 65-69° C. |
| Well done | gray-brown throughout; firm | 71-100° C. |
| Over cooked | blacken throughout; hard | >100° C. |

However, the temperature is only a physical indicator of the food in cooking, and the actual indicator for doneness extent is protein denaturation, i.e. the chemical status of the protein, which can provide more direct and precise information of the status of food based on established relation between doneness level and protein denaturation extent, also referred to as the protein status.

FIG. 1 schematically illustrates a high level flowchart of a method for controlling a cooking process of the food in accordance with one embodiment.

In step 110, the method obtains the protein status in the food in the course of heating the food. Here, the food refers to any kind of food that has protein as one of the dominant ingredients, such as beef, pork, egg, and the like. For purpose of explanation, the beef steak will be used to describe the embodiments herein by way of example.

There are four distinct levels of protein structure. In the tertiary structure, spatial arrangement is attained when a linear protein chain with secondary structure segments folds further into a compact three dimension (3D) form. Protein curls up on itself so that hydrophobic elements of the protein are buried deep inside the structure and hydrophilic elements end up on the outside. Some water molecules in food are bounded on the surface of protein by hydrophilic elements, e.g. hydrogen bonding. In the course of heating the food, the protein denaturation happens. In particular, the tertiary structure disrupts, leading to hydrophilic bonding breaks, and the bound water becomes free water. Also, the denaturation is accompanied by the release of calcium and magnesium ions.

As seen, during the protein denaturation, the bound water becomes free water, and ions are released. These two factors both largely change the dielectric property of the food. The protein denaturation process can be detected by measuring food dielectric property change. In other words, the protein status can be indicated by the dielectric behavior in the food.

The protein status of the food is obtained in a non-invasive way. In particular, the method emits a radio frequency (RF) signal to the food, which signal can penetrate into the food at a sufficient depth (e.g. centimeters) to detect the status of protein. The protein status of the food can be obtained by measuring the RF frequency absorption indicating the dielectric behavior in the food, which will be described in detail later.

In step 120, the method determines a doneness level of the food (at least partially) based on the protein status. Specifically, the doneness level of the food can be determined based on established relation between doneness level and the protein status. Herein, the protein status can be indicated in various ways, such as by the dielectric property change pattern, the spectrum characteristics of the RF signals suggesting the dielectric property in the food, as will be discussed later. For example, the method may search the database for the doneness level corresponding to the dielectric property change pattern (e.g. a curve shape) that indicates the protein status. For another example, the method may utilize the spectrum characteristics of the RF signals suggesting the dielectric property in the food to predict the doneness level of the food. The implementation of these embodiments will be discussed in detail later.

In step 130, the method controls the cooking process of the food (at least partially) based on the determined doneness level. For example, if the determined doneness level is equal to the target doneness level, the method may terminate the cooking process, and audibly or visually signal the user to remove the food from the cooking device. If the determined doneness level is approaching to the target one, the method may tune the cooking parameters of the apparatus/cooking device, including the heating power level, the duty cycle and the cooking time duration, so as to eventually reach the target doneness level without over-cooking.

The advantages of the method are embodied in the following aspects. In the first aspect, the proposed method offers an cooking solution more convenient in comparison with traditional methods where need user's input about target time/temperature. In this method, the user is only required to set a target doneness level of the food without inputting other cooking parameters such as temperature, cooking time etc, which is not easily grasped by an average user. As a result, it minimizes user intervention during cooking. In the second aspect, precise cooking control is enabled due to the direct indication of protein status during cooking. Temperature is a traditional indicator for cooking process. It is the cause of ingredient status change, but it is not the direct indicator of food status. In some cases, with salt, with different meat composition, with different personal preferences, and with different meat types, the temperature cannot give precise doneness information. By contrast, in this method, protein status is proposed as the indicator of food doneness, which facilitates to detect the food doneness more timely and accurately.

Furthermore, conductive food heating, such as frying, baking and grilling, involves a process of the heat transferring from the food surface to inside, which results in a negative temperature gradient to the center of the food. The core temperature of the food may be used to indicate the food doneness. In order to acquire the core temperature of the food, a temperature probe (e.g. thermocouple or thermal resistor) can be inserted into food to measure the core temperature. It is an invasive sensing technique, which can destroy the integrity of the food. Hence, it is desirable that the food doneness can be determined in a non-invasive way, which is made possible by involving the penetrative signal such as radio frequency signal in obtaining the protein status of the food.

As mentioned above, the protein status of the food in the course of heating the food can be indicated by the dielectric behavior in the food. The food dielectric behavior is dominated by several dielectric mechanisms. For radio frequencies, dipole orientation and ionic conduction are the main mechanisms. At the low RF frequencies, ionic conduction is the main effect. At the high radio frequencies, dipole orientation, which means that a polar molecule can adjust its direction according to an external electric field, contributes more. In the middle of RF frequencies, both of the two mechanisms are playing a part. The frequency relevance of food dielectric property is the basis of sensing the protein status of the food by radio frequency signals. Now, the process to obtain the protein status by RF signal, and thereby determine the food doneness in a non-invasive way, will be set forth with reference to FIG. 2.

Figure 2:
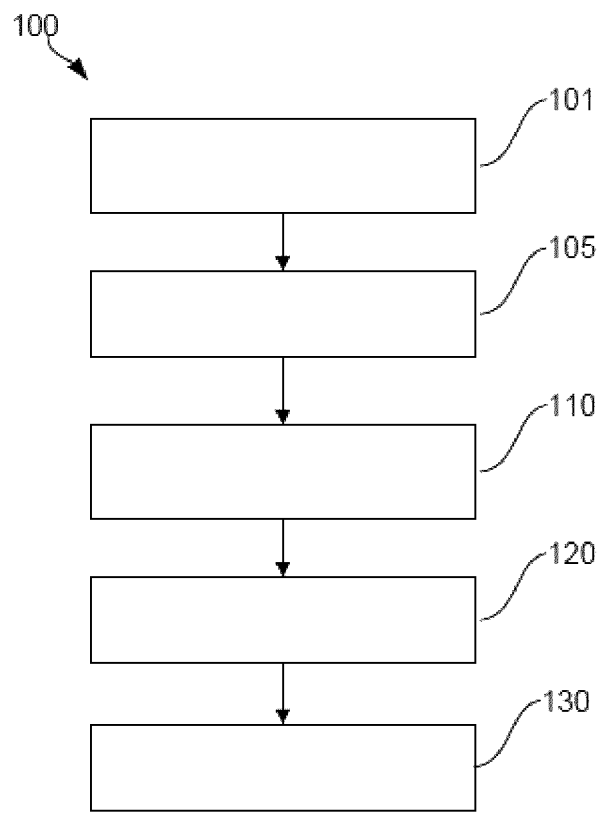
FIG. 2 schematically illustrates a flowchart of a method for controlling a cooking process of the food in accordance with an embodiment.

In FIG. 2, the method may emit a plurality of radio frequency signals into the food noninvasively continuously or discretely during heating the food at step 101, and receive a plurality of reflection signals or transmission signals of the radio frequency signals from the food at step 105. The reflection signals is a part of the radio frequency signals that reflect from inside of the food. The transmission signals is a part of the radio frequency signals that transmit through the food. Optionally, the reflection signals can be reflected from different depths of the food. As such, the reflections signals can indicate the energy absorption of RF signals at different depth of the food, which will help obtain the protein status of the food more accurately. Then, the method may obtain the protein status based on the plurality of radio frequency signals and the plurality of reflection signals or transmission signals at step 110. Specifically, the method can be implemented in the following ways:

Implementation I

The method may emit a plurality of radio frequency signals into the food at different points of time in the course of heating the food and receive the respective reflection signals or transmission signals. These radio frequency signals have the same frequency. The reason for emitting the plurality of radio frequency signals at different points of time in the course of heating is explained as below.

During the protein denaturation, the bound water becomes free water, and ions are released. These two factors both largely change the dielectric property of food. Hence, the protein denaturation process can be detected by measuring food dielectric property change. Specifically, in the initial stage of cooking (before protein denaturation), the increase in ionic mobility with temperature increase can lead to the increase in energy absorption of radio frequency. During protein denaturation, the increasing amount of free water and released ions largely accelerate the energy absorption of RF. At the later stage of denaturation, the water evaporation decreases the amount of free water and therefore decreases the ionic mobility, which results in decrease of RF energy absorption. As such, the dielectric property change in the food can be suggested by the change of the RF energy absorption during heating the food. In other words, the dielectric property of the food can be represented by the RF energy absorption, which can be quantized by scattering parameters such as $S_{11}$ and $S_{12}$, dielectric constant or loss factor.

Since the protein status can be indicated by the dielectric behavior, i.e. the dielectric property change during heating the food, in order to obtain the protein status, the method may calculate the dielectric properties over time based on the phases and/or amplitudes of the emitted radio frequency signals and the plurality of reflection signals or transmission signals at step 110. For example, the dielectric property can be represented by $S_{11}$, which is calculated as the ratio of the phase and/or amplitude of the emitted RF signal and the phase and/or amplitude of the corresponding reflection RF signal. For another example, the dielectric property can be represented by $S_{12}$, which is calculated as the ratio of the phase and/or amplitude of the emitted RF signal and the phase and/or amplitude of the corresponding transmission RF signal.

Subsequently, the method may determine the doneness level of the food based on the obtained dielectric properties at step 120. For example, the method may use the obtained dielectric properties to form a curve which illustrates the change of the dielectric property over time, and then match the shape of the curve with those predetermined curves indicating the individual doneness level to obtain the doneness level indicated by the curve.

Figure 3:
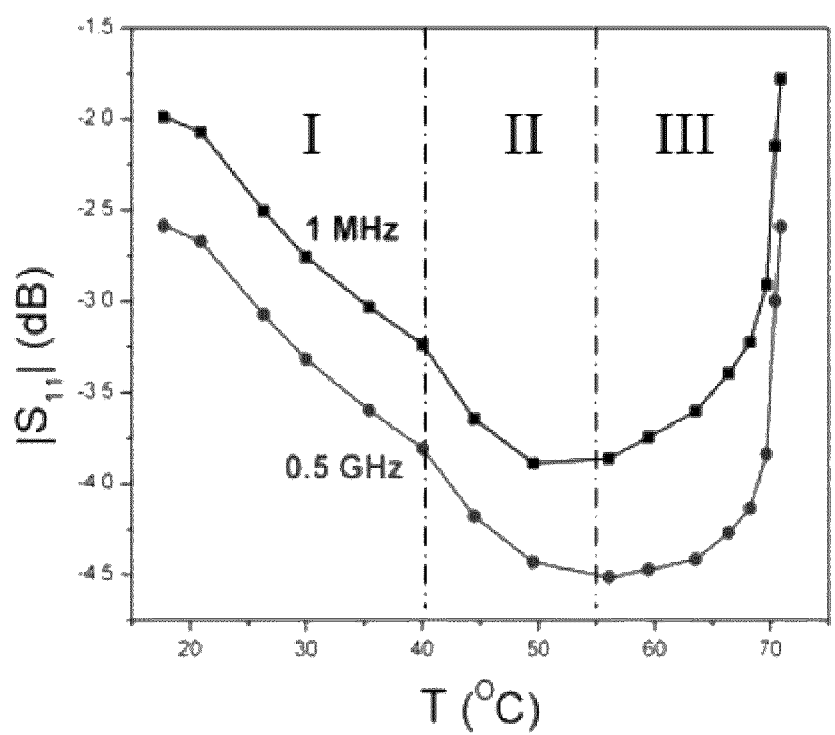
FIG. 3 is an exemplary diagram schematically illustrating the temperature dependence of dielectric property of the food.

The mapping between the predetermined curves and the individual doneness are illustrated in FIG. 3. FIG. 3 is an exemplary diagram schematically illustrating the temperature dependence of dielectric property of the beef steak. As shown, the horizontal axis is the temperature in Celsius, the vertical axis is the amplitude of $S_{11}$ in decibel. Two frequencies are selected representing of low frequency and high frequency cases. The upper curve is for 1 MHz, and the lower curve is for 0.5 GHz. The change of dielectric property in the beef steak can be divided into three stages. In the stage I (18-40° C.), the drop in $S_{11}$ is mainly due to the increase in ionic mobility which increases with temperature. In the stage II (40-55° C.), the temperature reaches the denaturation zone, and $S_{11}$ largely decreases because bound water changes into free water and myosin denaturation has been accompanied by the release of calcium and magnesium ions. In the stage III (55-70° C.), $S_{11}$ rebounds because the ionic mobility decreases due to water evaporation. As indicated, the shape of the curve indicating the dielectric property change has a dependency on the temperature, meanwhile the doneness levels for a beef steak corresponds to the respective temperature ranges. For example, 'medium rare' falls in 55-60° C., 'medium' falls in 60-65° C., and 'medium well' falls in 65-69° C. Hence, the mappings between the shape of the curve indicating the dielectric property change and the doneness level is established.

Figure 4:
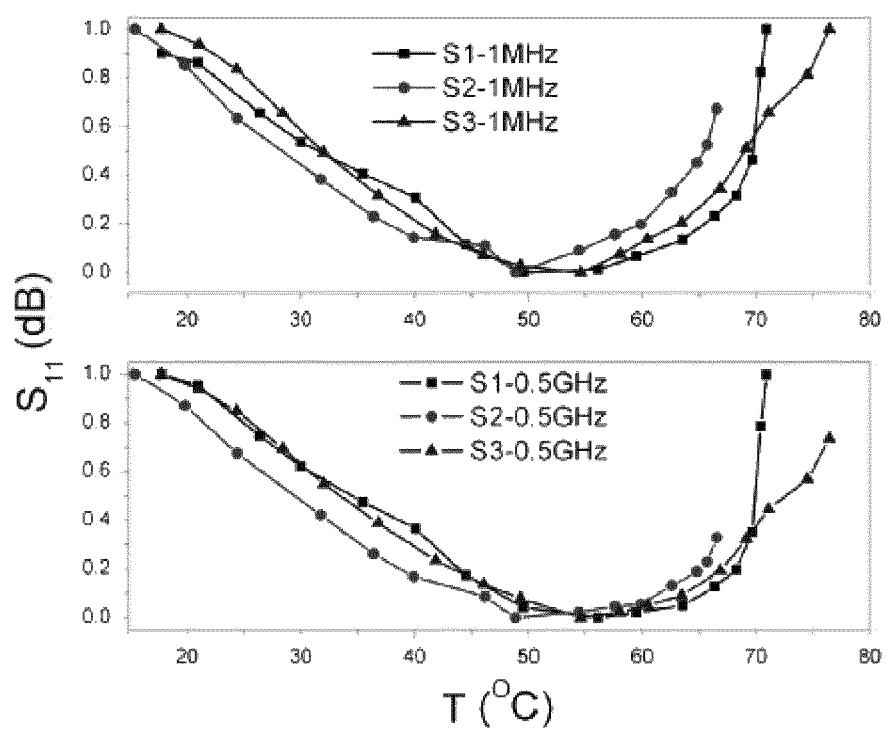
FIG. 4 is an exemplary diagram schematically illustrating the repeatability that the dielectric property of the food has dependence on the temperature.

Further, in order to prove the repeatability of the dielectric property change having dependency on temperature, three different types of beef steak were prepared and heated. The results are shown in FIG. 4. In order to compare the curves precisely, the curves were normalized to [0, 1]. The upper figure shows the results at 1 MHz, and the lower one shows that at 0.5 GHz. The similar profiles are shown (i.e. stage I-III), and it is shown that the curves have obvious repeatability.

As indicated, the shape of the curve indicating the change of dielectric property in food is featured by staged drop and rise associated with food doneness levels, which makes the determination of the doneness level of the food independent of the absolute measurement value, thereby protecting the determination of the doneness level against disturbing factors such as initial status of the food, composition variance in the food. This is an apparently advantage by comparison with measuring temperature (monotonically increasing) or moisture loss (monotonically decreasing).

Implementation II

After obtaining the dielectric properties as described in Implementation I, the method may also set up a function, denoted as f(t), based on the obtained dielectric properties. The f(t) is a function of the dielectric properties with respect to time. A derivative is taken for the f(t), and then normalized with respect to the f(t), whereby a function g(t) is derived, which can be formulated as:

$$g(t) = \frac{f'(t)}{f(t)}$$

As such, the method may calculate the value of g(t) at the current point of time, and then compare the calculated value with the predetermined threshold ranges indicating the individual doneness levels. In this way, the doneness level indicated by the calculated value can be determined.

Figure 5:
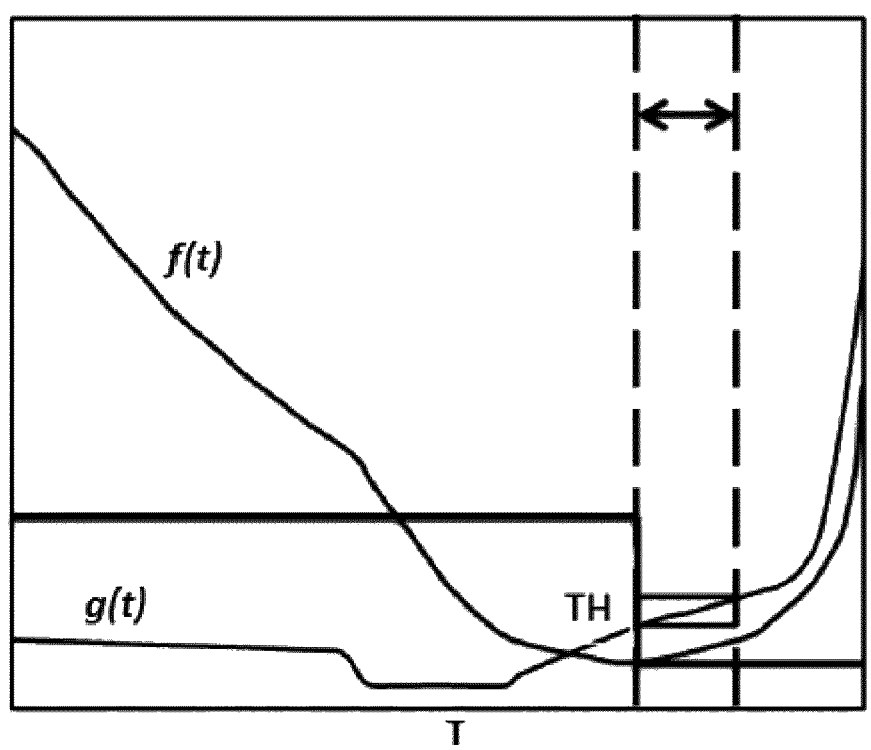
FIG. 5 is an exemplary diagram schematically illustrating the determination of the food doneness with the derivative scheme.

Now, the process to establish the predetermined threshold ranges indicating the individual doneness levels will be introduced with reference to FIG. 5. Taking the beef steak as example, a plurality of beef steak samples are used in training the threshold values. These beef steaks vary in kind, quality, size, and thickness. For each of the beef steaks, the change of the dielectric property during the heating is recorded, whereby the corresponding f(t) and thereby the g(t) can be recorded as illustrated in FIG. 5. Meanwhile, the doneness level will be marked along the curve g(t), which doneness level can be measured by invasive method (e.g. thermocouple) or provided by a professional chef. In this way, the threshold ranges indicating the individual doneness levels are identified for this sample. For example, the threshold range for doneness level i can be denoted as $TH_i=[TH_{i,lower}, TH_{i,upper}]$. As such, the resulting threshold range for the doneness level i can be calculated by averaging the identified threshold range for this doneness level of these samples.

Implementation III

The doneness level of the food can be predicted by the spectrum characteristics of the RF signals at multiple frequencies. In particular, the spectrum characteristics of the RF signals at multiple frequencies obtained at a specific point of time can be used in combination to predict the doneness level of the food at the specific time point.

In an embodiment, in order to determine the doneness level of the food at the current point of time, the method may emit a plurality of radio frequency signals into the food. These RF signals have at least two frequencies, which can be emitted concurrently or successively in a short time interval near the current point of time.

Then, the method may receive the respective reflection signals or transmission signals and extract parameters indicating the protein status in the food based on the plurality of emitted radio frequency signals and the plurality of reflection signals or transmission signals. The parameters refer to the spectrum characteristics of the RF signals, including, but not limited to, the magnitude and/or phase of the emitted radio frequency signals at different frequencies; the magnitude and/or phase of the reflection signals or transmission signals at different frequencies; the scattering parameters of the emitted radio frequency signals such as $S_{11}$ and $S_{12}$; the derivation information of the emitted RF signals, the reflection signals or transmission signals; the morphological information of these RF signals at multiple frequencies, for example, the ratio of the magnitudes/energies of the RF signals at the high frequency and the low frequency.

After extracting the parameters, the method may determine the doneness level of the food based on the extracted parameters. For example, the method may input the parameters as predicting variables into a doneness predictive model, and the predictive model can predict the doneness level based on the predicting variables. Here, the predictive model can be set up using data mining techniques, which includes Bayesian network, decision tree/random forest, neural network, k-Nearest Neighbor (k-NN) algorithm, and the like. For example, a large number of samples pairing the parameters (or features) extracted from the emitted RF signals, the reflection signals, or the transmission signals (denoted by $\vec{x}=\{x_1, x_2, \ldots x_n\}$) and the doneness level (denoted by C) will be trained using the k-NN algorithm to build up the doneness predictive model.

The introduction of multi-frequency information makes the sensing more robust against various disturbing factors including measurement error, electronic noise and food variation. Therefore, the food doneness can be determined accurately.

Figure 6:
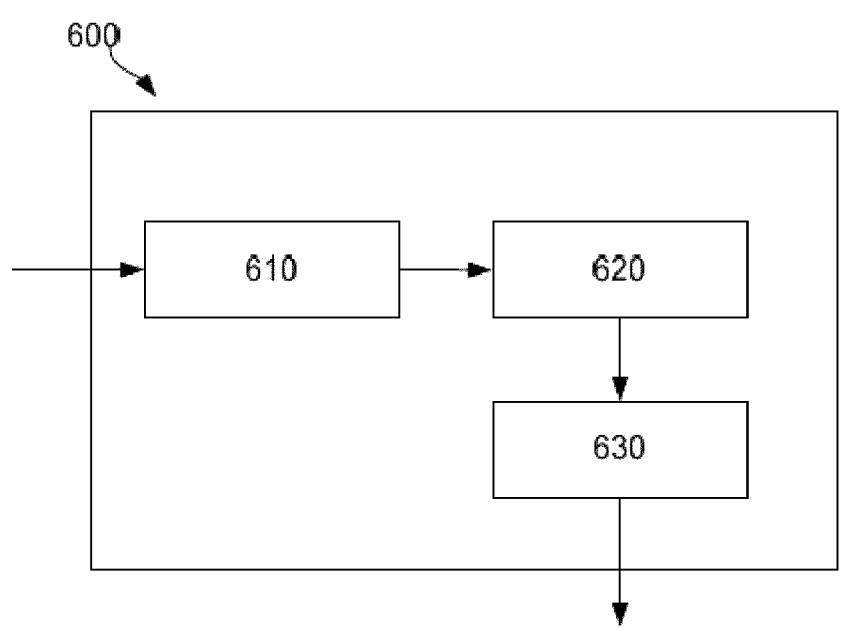
FIG. 6 is a block diagram of an apparatus configured to control a cooking process of food in accordance with an embodiment.

FIG. 6 is a block diagram of an apparatus configured to control a cooking process of food in accordance with one embodiment. As shown in FIG. 6, the apparatus 600 includes an obtaining unit 610, a determining unit 620 and a controlling unit 630. The apparatus 600 can work separately. It also can be partially or completely integrated into a cooking device. Now the functions of these elements will be described with reference to FIG. 6.

The obtaining unit 610 in the apparatus 600 obtains the protein status in the food in the course of heating the food. Here, the food refers to any kind of food that has protein as one of the dominant ingredients, such as beef, pork, egg, and the like.

The protein status of the food is obtained in a non-invasive way. In particular, the apparatus 600 may emit a penetrative signal such as radio frequency wave to the food, which penetrative signal can penetrate into the food at a sufficient depth (e.g. centimeters) to detect the status of protein. Therefore, the obtaining unit 610 can obtain the protein status of the food by measuring the RF frequency absorption reflecting the dielectric behavior in the food, which will be described in detail later.

The determining unit 620 in the apparatus 600 determines a doneness level of the food (at least partially) based on the protein status. Specifically, the doneness level of the food can be determined based on established relation between doneness level and the protein status. Herein, the protein status can be indicated in various ways, such as by the dielectric property change pattern, the spectrum characteristics of the RF signals suggesting the dielectric property in the food, as will be discussed later. For example, the determining unit 620 may search the database for the doneness level corresponding to the dielectric property change pattern (e.g. a curve line) that indicates the protein status. For another example, the determining unit 620 may utilize the spectrum characteristics of the RF signals suggesting the dielectric property in the food to predict the doneness level of the food. The implementation of these embodiments will be discussed in detail later.

The controlling unit 630 in the apparatus 600 controls the cooking process of the food (at least partially) based on the determined doneness level. For example, if the determined doneness level is equal to the target doneness level, the controlling unit 630 may terminate the cooking process, and audibly or visually signal the user to remove the food from the cooking device. If the determined doneness level is approaching to the target one, the controlling unit 630 may tune the cooking parameters of the cooking device, including the heating power level, the duty cycle and the cooking time, so as to eventually reach the target doneness level without over-cooking.

The advantages of the embodiment are embodied in the following aspects. In the first aspect, it offers an automatic cooking solution in comparison with traditional methods that need user's input about target time/temperature. In this embodiment, the user is only required to set a target doneness level of the food without inputting other cooking parameters such as temperature, cooking time etc, which is not easily grasped by an average user. As a result, it minimizes user intervention during cooking. In the second aspect, precise cooking control is enabled due to the direct indication of protein status during cooking. Temperature is a traditional indicator for cooking process. It is the cause of ingredient status change, but it is not the direct indicator of food status. In some cases, with salt, with different meat composition, with different personal preferences, and with different meat types, the temperature cannot give precise doneness information. By contrast, in this embodiment, protein status is proposed as the indicator of food doneness, which facilitates to detect the food doneness more timely and accurately.

Furthermore, conductive food heating, such as frying, baking and grilling, involves a process of the heat transferring from the food surface to inside, which results in a negative temperature gradient to the center of the food. Thus, traditionally the core temperature of the food is used to indicate the food doneness. In order to acquire the core temperature of the food, it is often that the temperature probe (e.g. thermocouple or thermal resistor) is inserted into food to measure the core temperature. It is an invasive sensing technique, which can destroy the integrity of the food. Hence, it is desirable that the food doneness can be determined in a non-invasive way, which is made possible by involving the penetrative signal such as radio frequency signal in obtaining the protein status of the food.

Figure 7:
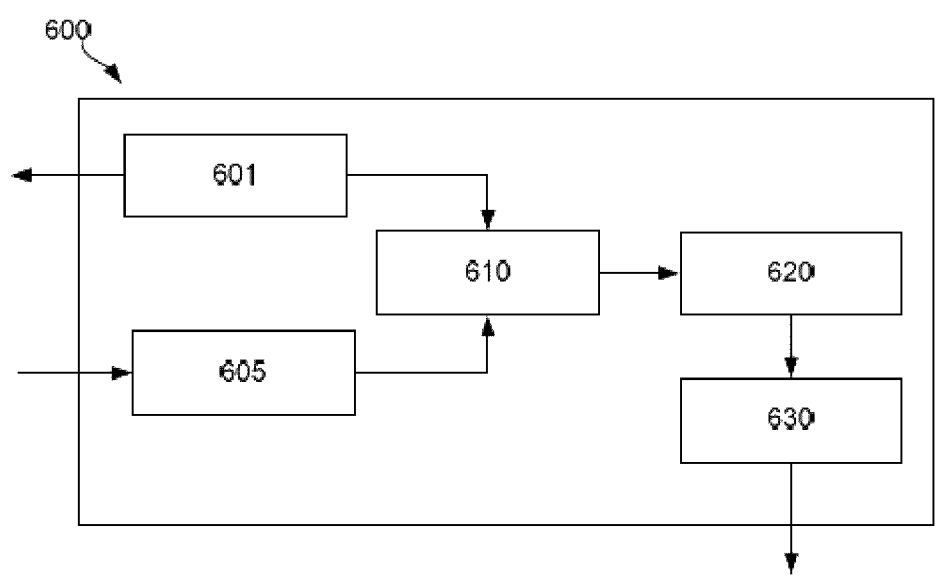
FIG. 7 schematically illustrates a block diagram of an apparatus configured to control a cooking process of food in accordance with an embodiment.

In order to achieve this object, the apparatus 600 comprises an emitting unit 601 and a receiving unit 605 as illustrated in FIG. 7.

The emitting unit 601 in the apparatus 600 emits a plurality of radio frequency signals into the food noninvasively. For example, the emitting unit 601 can be an open-ended coaxial probe. The probe may keep touch with the food when emitting the RF signal. Alternatively, the probe may not contact with the food while emitting the RF signal, as long as the emitted RF signal can penetrate into the food up to a depth sufficient to detect the protein status.

The receiving unit 605 may accordingly receive a plurality of reflection signals or transmission signals of the radio frequency signals from the food. The reflection signals is a part of the radio frequency signals that reflect from inside of the food. The transmission signals is a part of the radio frequency signals that transmit through the food. Optionally, the reflection signals can be reflected from different depths of the food. As such, the reflections signals can indicate the energy absorption of RF signals at different depth of the food, which will help obtain the protein status of the food more accurately.

When the receiving unit 605 is configured to receive the reflection signals, it can be placed on the same side of the food. In this case, the receiving unit 605 and the obtaining unit 601 can be integrated together as a single element. Additionally or alternatively, when the receiving unit 605 is configured to receive the transmission signal, it will be placed on the other side of the food in opposition to the emitting unit 601.

Subsequently, the obtaining unit 610 may obtain the protein status based on the plurality of radio frequency signals emitted by the emitting unit 601 and the plurality of reflection signals or transmission signals received by the receiving unit 605.

These units in the apparatus 600 may collaborate in the following ways to determine the doneness level of the food:

Implementation I

The emitting unit 601 may emit a plurality of radio frequency signals into the food at different points of time in the course of heating the food and the receiving unit 605 may receive the respective reflection signals or transmission signals. These RF signals have the same frequency. The RF signals can be emitted and received continuously or discretely during heating the food.

In order to obtain the protein status, the obtaining unit 610 may calculate the dielectric properties over time based on the phases and/or amplitudes of the emitted radio frequency signals and the plurality of reflection signals or transmission signals. For example, the dielectric property can be represented by $S_{11}$, which is calculated as the ratio of the phase and/or amplitude of the emitted RF signal and the phase and/or amplitude of the corresponding reflection RF signal. For another example, the dielectric property can be represented by $S_{12}$, which is calculated as the ratio of the phase and/or amplitude of the emitted RF signal and the phase and/or amplitude of the corresponding transmission RF signal.

The determining unit 620 may determine the doneness level of the food based on the obtained dielectric properties. For example, the method may use the obtained dielectric properties to form a curve which illustrates the change of the dielectric property over time, and then match the shape of the curve with those predetermined curves indicating the individual doneness level to obtain the doneness level indicated by the curve.

As mentioned above, the shape of the curve indicating the change of dielectric property in food is featured by staged drop and rise associated with food doneness levels, which makes the determination of the doneness level of the food independent of the absolute measurement value, thereby protecting the determination of the doneness level against disturbing factors.

Implementation II

After obtaining the dielectric properties as described in Implementation I, the obtaining unit 610 may also set up a function, denoted as f(t), based on the obtained dielectric properties. The f(t) is a function of the dielectric properties with respect to time. A derivative is taken for the f(t), and then normalized with respect to the f(t), whereby a function g(t) is derived, which can be formulated as:

$$g(t) = \frac{f'(t)}{f(t)}$$

As such, the obtaining unit may calculate the value of g(t) at the current point of time, and then the determining unit may compare the calculated value with the predetermined threshold ranges indicating the individual doneness levels. In this way, the doneness level indicated by the calculated value can be determined.

Implementation III

The emitting unit 601 may emit a plurality of radio frequency signals into the food. These RF signals have at least two frequencies, which can be multiple separated frequency points, a frequency band, or combination thereof. They can be emitted concurrently or successively in a short time interval. Then, the receiving unit 605 may receive the respective reflection signals or transmission signals.

The obtaining unit 610 may extract parameters indicating the protein status in the food based on the plurality of emitted radio frequency signals and the plurality of reflection signals or transmission signals. The parameters refer to the spectrum characteristics of the dielectric property in the food, including, but not limited to, the magnitude and/or phase of the emitted radio frequency signals at different frequencies; the magnitude and/or phase of the reflection signals or transmission signals at different frequencies; the scattering parameters of the emitted radio frequency signals such as $S_{11}$ and $S_{12}$; the derivation information of the emitted RF signals, the reflection signals or transmission signals; and the morphological information of these RF signals at multiple frequencies, for example, the ratio of the magnitudes/energies of the RF signals at the high frequency and the low frequency.

The determining unit 620 may determine the doneness level of the food based on the extracted parameters. For example, the determining unit 620 may input the parameters as predicting variables into a doneness predictive model, and the predictive model can predict the doneness level based on the predicting variables. Here, the predictive model can be set up using data mining techniques as described above.

The introduction of multi-frequency information makes the sensing more robust against various disturbing factors including measurement error, electronic noise and food variation. Therefore, the food doneness can be determined accurately.

In addition, as known, conductive food heating involves a process of the heat transferring from the food surface to inside. Hence, it may occur that when the core reaches a desired doneness level, the other parts, especially those at corners and close to edge, are overcooked. The extent of overcooking increases with the size and thickness of a beef steak. Undercooking happens with an irregular food shape or uneven food composition distribution. In these cases, although the core is cooked to a proper doneness level, over- or undercooking at other parts may affect on overall taste and mouth-feel (stiff, less juicy etc). Thus, it is desirable that the overall doneness level of the food can be determined by taking into account its spatial unevenness.

Figure 8:
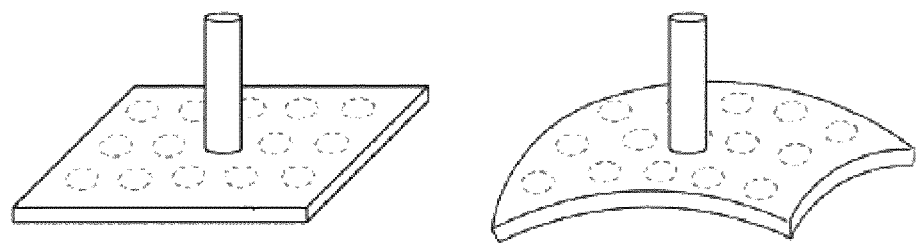
FIG. 8 schematically illustrates the arrangements of the array of radio frequency sensing probes in accordance with an embodiment.
Figure 9:
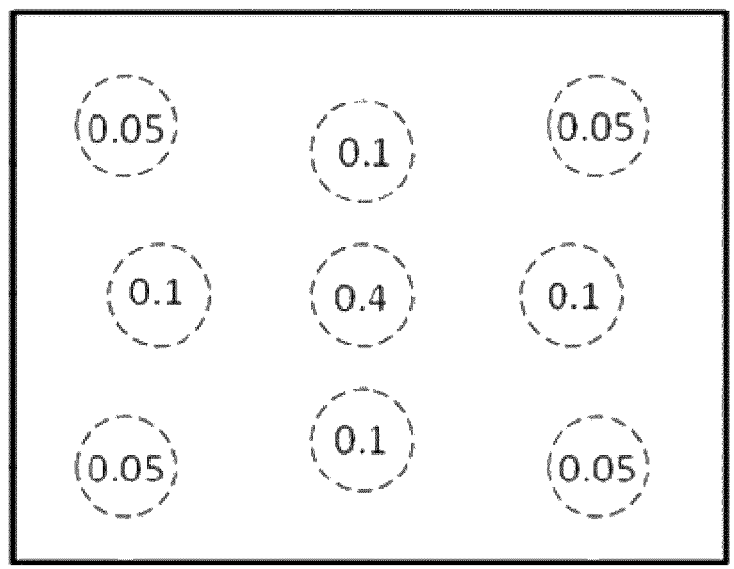
FIG. 9 schematically illustrates an example of setting weighting efficient for the array of RF sensing probes in determining the doneness level of the food.

In order to achieve this object, the apparatus 600 may comprise a plurality of pairs of the emitting unit 601 and the receiving unit 605, each of which may emit a plurality of radio frequency signals into different parts of the food and receive the respective reflection signals or transmission signals therefrom. For example, the plurality of pairs of the emitting unit 601 and the receiving unit 605 are an array of open-ended coaxial probes. The probes can be arranged inside one plane or following a specific curvature, as illustrated in FIG. 8. If the probes keep touch with the food in operation, a curved surface may lead to better contact and therefore improved signal to noise ratio (SNR) of detection. The probes can be equidistantly placed or arranged in a specific pattern as desired.

The obtaining unit 610 may obtain protein statuses in the different parts of the food based on the radio frequency signals and the plurality of reflection signals or transmission signals for the individual parts.

Then the determining unit 630 may determine doneness levels of the different parts of the food based on the respective protein statuses, and calculate the doneness level of the food by weighing the doneness levels of the different parts of the food. The overall doneness level of the food can be generally described by a function as below:

$$DL_{overall} = f(DL_1, DL_2, 1, DL_N)$$

where $DL_{overall}$ represents the overall doneness level, and $DL_i(i-1, 1, N)$ represents the doneness level for individual parts of the food.

By way of example, the $DL_{overall}$ can be calculated by the formula as below:

$$DL_{overall} = \text{round}\left(\sum_{i=1}^{N} w_i DL_i\right) \quad (1)$$

where $w_i$ is the weighing factor of the doneness level $DL_i$, round(x) is to take an integer closest to x. Take beef steak frying as an example, in order to be mathematically operational, the doneness level $DL_i$ is assigned with integer numbers from 1 to 5 that are defined by {1='rare', 2='medium rare', 3='medium', 4='medium well', 5='well done'}.

Setting of the weighing factor $w_i$ is based on the relevance of a local doneness level to the overall one. The doneness of the core is most important, as it is used traditionally as a defining criterion, so the weighing factor can be set the highest. In common sense, the doneness degree gets less important when moving away from the core towards corners and edges. The $w_i$ therefore can be set in a descending order accordingly.

An example of the weighing factor value setting is given in FIG. 4. Assuming the doneness levels detected by the nine probes are Central probe: 'medium'=3;
Edge probe: 'medium well'=4;
Corner probe: 'well done'=5.
Then the overall doneness calculated according to formula (1) is $$DL_{overall} = \text{round}(0.4 \times 3 + 4 \times 0.1 \times 4 + 4 \times 0.05 \times 5) = 4,$$

i.e. medium well. This example shows that the overall doneness is better determined as 'medium well' despite 'medium' at the center, taking into account the actual doneness degree of the four relatively large edge areas.

Doneness levels from individual probes can be given fractional values in order to allow a higher doneness 'resolution' in the intermediate calculation, for instance, 3.5 for a status between 'medium' and 'medium well'.

The present disclosure also proposes a cooking device comprising the apparatus configured to control a cooking process of food as described above. The emitting unit and the receiving unit in the apparatus can be arranged into the cooking device as appropriate, such as on lid of the cooking device, at bottom of the cooking device, etc.

By way of example, the arrangements of the emitting unit and the receiving unit in the cooking device are illustrated in FIG. 10. The emitting unit and the receiving unit are illustrated by small black squares. The food ingredients is illustrated by hatched rectangle.

Figure 10A:
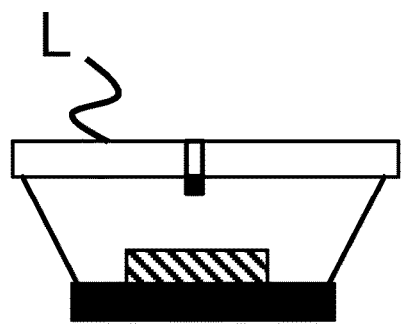
FIG. 10 schematically illustrates the arrangements of the RF sensing probe in the cooking device in accordance with an embodiment.

In FIG. 10(a), both the emitting unit and the receiving unit are placed on lid (L) of the cooking device. The receiving unit may receive the reflection signals. They don't have contact with the food in operation.

Figure 10B:
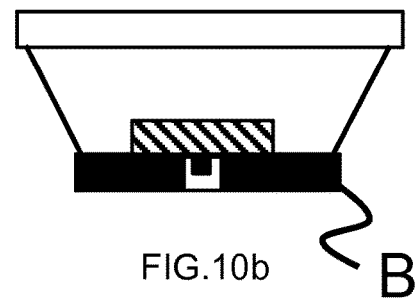

In FIG. 10(b), both the emitting unit and the receiving unit are placed at the bottom (B) of the cooking device, i.e. under the food. They have contact with the food in operation.

Figure 10C:
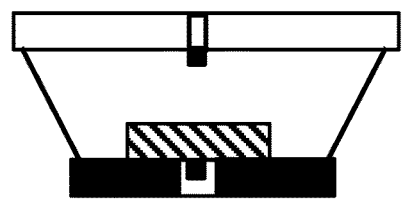

In FIG. 10(c), one of the emitting unit and the receiving unit is placed at the bottom of the cooking device, the other one is placed on lid of the cooking device. The receiving unit may receive the transmission signals.

Figure 10D:
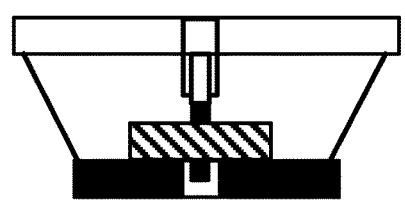

In FIG. 10(d), the arrangement is similar to FIG. 10(c) except that both the emitting unit and the receiving unit have contact with the food in operation.

Figure 10E:
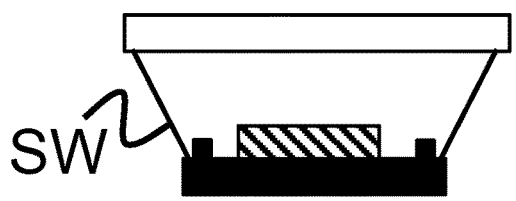

In FIG. 10(e), the emitting unit and the receiving unit are placed at the bottom of the side wall (SW) of the cooking device in opposition to each other. As such, the food is placed between the emitting unit and the receiving unit. The emitting unit emits the RF signals into the food from a side of the food, and the receiving unit receives the transmission RF signals propagating through the food from another side of the food.

Figure 10F:
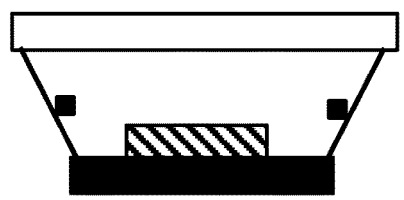

Alternatively, the emitting unit and the receiving unit can be placed in the middle of the side wall of the cooking device in opposition to each other as illustrated in FIG. 10(f). In this case, the RF signals emitted by the emitting unit will graze through the food, and the scattered signals will be received by the receiving unit. This is especially applicable for the food that is too thick to be transmitted by the RF signals.

While the embodiments have been illustrated and described herein, it will be understood by those skilled in the art that various changes and modifications may be made, any equivalents may be substituted for elements thereof without departing from the true scope of the present technology. In addition, many modifications may be made to adapt to a particular situation and the teaching herein without departing from its central scope. Therefore it is intended that the present embodiments not be limited to the particular embodiment disclosed as the best mode contemplated for carrying out the present technology, but that the present embodiments include all embodiments falling within the scope of the appended claims.

The invention claimed is:

1. A method for controlling a cooking process of food, comprising steps of:
   emitting a plurality of radio frequency signals into the food noninvasively at different points of time in the course of heating the food, wherein the plurality of radio frequency signals have a same frequency;
   receiving from the food a plurality of second radio frequency signals taken among the set defined by reflection signals and transmission signals, wherein the reflection signals comprise a part of the radio frequency signals that reflect from the food, and the transmission signals comprise a part of the radio frequency signals that transmit through the food;
   obtaining a protein status, wherein the protein status is an extent of protein denaturation, in the food in the course of heating the food, based on dielectric properties of the food, the dielectric properties being determined based on phases or amplitudes of (i) the plurality of radio frequency signals and (ii) the plurality of second radio frequency signals;
   determining a doneness level of the food based on the protein status, wherein the determining step comprises determining the doneness level corresponding to a change of the dielectric properties featured by a staged drop and rise associated with food doneness levels, wherein dielectric properties obtained over time form a curve, that illustrates the change in dielectric properties over time, and a shape of the curve is matched to at least one predetermined curve of a plurality of predetermined curves, each predetermined curve indicating an individual doneness level, to obtain the doneness level indicated by the curve; and
   controlling the cooking process of the food based on the determined doneness level.

2. The method of claim 1, wherein the dielectric properties are represented by scattering parameters, dielectric constant or loss factor.

3. A non-transitory computer readable storage medium embodied with instructions which, when executed on an apparatus, cause the apparatus to perform the steps of the method according to claim 1.

4. The method of claim 1, wherein emitting and receiving comprises emitting and receiving with a plurality of pairs of an emitting unit and a receiving unit that comprise an array of open-ended coaxial probes, for emitting a plurality of RF signals into different parts of the food and for receiving respective reflection or transmission signals therefrom, wherein the array of open-ended coaxial probes are arranged in one plane or follow a specific curvature, further wherein obtaining the protein status includes obtaining the protein status in the different parts of the food, and further wherein determining the doneness level includes determining doneness levels of the different parts of the food based on respective protein statuses and calculating the doneness level of the food by weighting the doneness levels of the different parts of the food.

5. An apparatus configured to control a cooking process of food, comprising:
   an emitting unit adapted to emit a plurality of radio frequency signals into the food noninvasively;
   a receiving unit adapted to receive from the food a plurality of second radio frequency signals taken among the set defined by reflection signals and transmission signals, wherein the reflection signals comprise a part of the radio frequency signals that reflect from the food, and the transmission signals comprise a part of the radio frequency signals that transmit through the food;
   an obtaining unit adapted to obtain a protein status in the food in the course of heating the food, wherein the protein status comprises an extent of protein denaturation in the food, based on (i) the plurality of radio frequency signals and (ii) the plurality of second radio frequency signals;
   a determining unit adapted to determine a doneness level of the food based on the protein status; and
   a controlling unit adapted to control, at least partially, the cooking process of the food based on the determined doneness level,
   wherein the plurality of radio frequency signals have a same frequency, wherein the emitting unit is adapted to emit the plurality of radio frequency signals into the food at different points of time in the course of heating the food,
   wherein the obtaining unit is further adapted to obtain the protein status based on dielectric properties of the food, the dielectric properties being determined based on phases or amplitudes of (i) the radio frequency signals and (ii) the plurality of second radio frequency signals, and
   wherein the determining unit is further adapted to determine the doneness level of the food based on a change of the dielectric properties over time featured by a staged drop and rise associated with food doneness levels, wherein dielectric properties obtained over time form a curve, that illustrates the change in dielectric properties over time, and a shape of the curve is matched to at least one predetermined curve of a plurality of predetermined curves, each predetermined curve indicating an individual doneness level, to obtain the doneness level indicated by the curve.

6. The apparatus of claim 5, wherein emitting unit and the receiving unit comprise a plurality of pairs of an emitting unit and a receiving unit that comprise an array of open-ended coaxial probes, for emitting a plurality of RF signals into different parts of the food and for receiving respective reflection or transmission signals therefrom, wherein the array of open-ended coaxial probes are arranged in one plane or follow a specific curvature, further wherein the obtaining unit is further adapted to obtain the protein status in the different parts of the food, and further wherein the determining unit is further adapted to determine the doneness levels of the different parts of the food based on respective protein statuses and calculate the doneness level of the food by weighting the doneness levels of the different parts of the food.

7. The apparatus of claim 5, wherein:
the emitting unit and the receiving unit comprise a plurality of pairs of the emitting unit and the receiving unit, wherein the plurality of emitting units are adapted to emit a plurality of radio frequency signals into different parts of the food;
the obtaining unit is adapted to obtain protein statuses in the different parts of the food based on the radio frequency signals and the plurality second radio frequency signals for the individual parts; and
the determining unit is adapted to (i) determine doneness levels of the different parts of the food based on the respective protein statuses, and (ii) calculate the doneness level of the food by weighing the doneness levels of the different parts of the food.

8. The apparatus of claim 5, wherein the controlling unit is further adapted to tune parameters of the apparatus, wherein the parameters of the apparatus include at least one selected from the group consisting of (i) heating power level, (ii) duty cycle and (iii) a cooking time duration.

9. A cooking device, comprising an apparatus configured to control a cooking process of food according to claim 5.

10. The cooking device of claim 9, wherein the emitting unit and the receiving unit of the apparatus are placed on a lid of the cooking device.

11. The cooking device of claim 9, wherein the emitting unit and the receiving unit of the apparatus are placed at the bottom of the cooking device.

\* \* \* \* \*